United States Patent
Mahajan et al.

(10) Patent No.: US 11,631,478 B2
(45) Date of Patent: Apr. 18, 2023

(54) PRIORITY-BASED MEDICAL DATA MANAGEMENT SYSTEM

(71) Applicant: Cardiac Pacemakers, Inc., St. Paul, MN (US)

(72) Inventors: Deepa Mahajan, North Oaks, MN (US); David L. Perschbacher, Coon Rapids, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 392 days.

(21) Appl. No.: 16/025,855

(22) Filed: Jul. 2, 2018

(65) Prior Publication Data
US 2019/0013087 A1 Jan. 10, 2019

Related U.S. Application Data

(60) Provisional application No. 62/528,692, filed on Jul. 5, 2017.

(51) Int. Cl.
*G16H 10/60* (2018.01)
*G16H 50/20* (2018.01)
(Continued)

(52) U.S. Cl.
CPC .............. *G16H 10/60* (2018.01); *A61N 1/37* (2013.01); *A61N 1/37252* (2013.01); *G16H 50/20* (2018.01); *A61N 1/37282* (2013.01)

(58) Field of Classification Search
CPC ... G06F 1/00–2221/2153; G16H 10/00–80/00; A61N 1/00–2007/027
See application file for complete search history.

(56) References Cited

U.S. PATENT DOCUMENTS 9,597,525 B2 * 3/2017 Cao ........................ A61B 5/0452
2004/0141661 A1 * 7/2004 Hanna ..................... G06Q 10/10
382/305

(Continued)

FOREIGN PATENT DOCUMENTS

CN 111093759 A 5/2020
JP 2006043152 * 2/2006 ............... A61B 5/00
WO WO-2019010133 A1 1/2019

OTHER PUBLICATIONS

Gregory Engel, "Remote Monitoring for Atrial Fibrillation," Congestive Heart Failure, vol. 14, Issue s2, pp. 14-18. (Year: 2008).*

(Continued)

*Primary Examiner* — Jonathon A. Szumny
(74) *Attorney, Agent, or Firm* — Schwegman Lundberg & Woessner, P.A.

(57) ABSTRACT

Systems and methods for managing medical information storage and transmission are discussed. A data management system may include a receiver circuit to receive information about a physiological event sensed from a patient, and an event prioritizer circuit to assign a priority to the received information. A control circuit may perform data reduction of the received information according to the assigned priority. Data reduction at a higher reduction rate is performed on the received information if a lower priority is assigned than if a higher priority is assigned. The system may include an output circuit to output the received information to a user or a process, or to transmit the received information to an external device, according to the assigned priority.

20 Claims, 4 Drawing Sheets

(51) Int. Cl.
*A61N 1/372* (2006.01)
*A61N 1/37* (2006.01)

(56) References Cited

U.S. PATENT DOCUMENTS

| | | | |
|---|---|---|---|
| 2004/0158299 A1 | 8/2004 | Patrias | |
| 2006/0253042 A1* | 11/2006 | Stahmann | A61B 5/02405 600/508 |
| 2007/0183493 A1* | 8/2007 | Kimpe | H04N 19/37 375/240.1 |
| 2008/0058651 A1 | 3/2008 | Shen et al. | |
| 2009/0058635 A1 | 3/2009 | LaLonde et al. | |
| 2009/0069642 A1* | 3/2009 | Gao | G06F 19/3418 600/300 |
| 2009/0082640 A1* | 3/2009 | Kovach | A61B 5/7435 600/300 |
| 2009/0248438 A1* | 10/2009 | Tyler | G06Q 10/10 705/2 |
| 2011/0075950 A1* | 3/2011 | Ohashi | G06K 9/4642 382/305 |
| 2011/0082377 A1* | 4/2011 | Mahajan | A61B 5/7232 600/508 |
| 2011/0295560 A1* | 12/2011 | Crockford | G06F 19/3418 702/187 |
| 2013/0147622 A1* | 6/2013 | LaLonde | G06F 19/3418 340/539.12 |
| 2013/0158361 A1* | 6/2013 | Bardy | A61B 5/0022 600/300 |
| 2015/0067021 A1* | 3/2015 | Protas | H04L 67/16 709/202 |
| 2015/0080674 A1 | 3/2015 | Drew et al. | |
| 2015/0227710 A1* | 8/2015 | Pappada | G16H 70/20 705/2 |
| 2016/0098539 A1* | 4/2016 | Zamanakos | G16H 10/60 705/3 |
| 2016/0328526 A1* | 11/2016 | Park | G16Z 99/00 |
| 2017/0092011 A1* | 3/2017 | Oikawa | G06T 7/73 |
| 2017/0136164 A1* | 5/2017 | Yeatts | A61M 60/585 |
| 2017/0269985 A1* | 9/2017 | Xiao | G06F 16/24578 |
| 2018/0004908 A1* | 1/2018 | Barrus | H04W 24/08 |
| 2018/0021590 A1* | 1/2018 | Allavatam | A61B 5/0245 607/28 |

OTHER PUBLICATIONS

"European Application Serial No. 18743368.5, Response to Communication Pursuant to Rules 161 and 162 filed Aug. 17, 2020", 13 pgs.

"International Application Serial No. PCT/US2018/040630, International Preliminary Report on Patentability dated Jan. 16, 2020", 7 pgs.

"International Application Serial No. PCT/US2018/040630, International Search Report dated Sep. 26, 2018", 5 pgs.

"International Application Serial No. PCT/US2018/040630, Written Opinion dated Sep. 26, 2018", 5 pgs.

* cited by examiner

PRIORITY-BASED MEDICAL DATA MANAGEMENT SYSTEM

CLAIM OF PRIORITY

This application claims the benefit of priority under 35 U.S.C. § 119(e) of U.S. Provisional Patent Application Ser. No. 62/528,692, filed on Jul. 5, 2017, which is herein incorporated by reference in its entirety.

TECHNICAL FIELD

This document relates generally to medical devices, and more particularly, to systems, devices and methods for managing medical data storage and transmission.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac electrostimulation therapies to treat cardiac arrhythmias or to rectify cardiac dyssynchrony in CHF patients.

The IMDs may store in a storage device medical data associated with detected physiological events such as a cardiac arrhythmia or worsening heart failure (WHF). The IMDs may be interconnected to a patient management system via a data communication network. Device data, such as the medical data associated with the detected physiological events, may be transmitted to a patient management system, through which a healthcare professional may remotely follow up with the patients or assess functions of the IMDs on a regular basis.

OVERVIEW

A patient management system may manage a large volume of alert notifications corresponding to physiological events detected from ambulatory medical devices (AMDs). For example, in managing AMD patients in a clinic, the patient management system may frequently receive alert notifications on various cardiac arrhythmia episodes or worsening heart failure (WHF) events detected by the AMDs, such as a cardiac monitor, a pacemaker, an implantable defibrillator, or a cardiac resynchronization therapy device. Physiological data associated with the alerts may be stored in the AMDs, transmitted to the patient management system, and reviewed by a clinician for the purpose of, for example, adjudicating the device-detected physiological events, scheduling patient follow-up visits, or reprogramming the AMDs, among others.

Management of a large amount of device-collected medical data, such as processing, storage, and transmission of such data, can be challenging to the patient management system as well as the clinicians and the healthcare facilities. The AMDs, such as implantable medical devices, may have limited battery power, storage space, computing and information processing power, or communication bandwidth. Data processing, storage, and transmission may require substantial amount of system resources. Clinician review of the device-detected events requires significant amount of time and resources, and can be costly or otherwise time consuming for a healthcare facility. On the other hand, device-detected physiological events may be of different degrees of severity or clinical significance. For example, some physiological events may contain diagnostic information not presented in patient historical physiological events or not reviewed and evaluated by the clinician. Configurable evaluation and prioritization of the physiological events may provide a technical solution to the power and resource constraints in AMD for processing high-volume device data, and improve the efficiency of clinician review and adjudication of the physiological events.

This document discusses, among other things, systems, devices, and methods for managing medical data storage and transmission. A data management system may include a receiver circuit to receive medical data associated with a physiological event sensed from a patient, and an event prioritizer circuit to assign a priority to the received information. A control circuit may perform data reduction of the received information according to the assigned priority. Data reduction at a higher reduction rate is performed on the received information assigned with a low priority than the received information assigned with a high priority. The system may output the physiological event to a user or a process according to the assigned priority.

Example 1 is a system that comprises a receiver circuit, an event prioritizer circuit, and a control circuit. The receiver circuit may receive information about a physiological event sensed from a patient. The event prioritizer circuit may assign a priority to the received information. The control circuit may perform a first data reduction of the received information if a high priority is assigned, and perform a second data reduction of the received information if a low priority is assigned. The second data reduction has a higher data reduction rate than the first data reduction.

In Example 2, the subject matter of Example 1 optionally includes the event prioritizer circuit that may assign the priority to the received information using a comparison of the received information and information from one or more patient historical physiological events.

In Example 3, the subject matter of Example 2 optionally includes the event prioritizer circuit that may receive a priority indication of the one or more patient historical physiological events from a user.

In Example 4, the subject matter of any one or more of Examples 2-3 optionally includes the event prioritizer circuit that may compute a similarity metric between the received information and information from one or more patient historical physiological events, and assign a high priority to the received information if the computed similarity metric falls below a threshold, and to assign a low priority to the received information if the computed similarity metric exceeds the threshold.

In Example 5, the subject matter of any one or more of Examples 1-4 optionally includes a data storage circuit that may store the received information according to the assigned priority.

In Example 6, the subject matter of Example 5 optionally includes the control circuit that may allocate storage space for storing the received information in the data storage circuit according to the assigned priority.

In Example 7, the subject matter of any one or more of Examples 1-6 optionally includes an ambulatory medical device (AMD) including one or more of the receiver circuit, the event prioritizer circuit, and the control circuit.

In Example 8, the subject matter of Example 7 optionally includes the AMD that is operatively in communication with an external device. The AMD may include the control circuit further configured to transmit the received information to the external device according to the assigned priority.

In Example 9, the subject matter of Example 8 optionally includes the control circuit that may allocate communication bandwidth for transmitting the received information according to the assigned priority.

In Example 10, the subject matter of any one or more of Examples 1-9 optionally includes the control circuit that may compress the received information at a first compression ratio if a high priority is assigned, and compress the received information at a second, higher compression ratio if a low priority is assigned.

In Example 11, the subject matter of any one or more of Examples 1-10 optionally includes the control circuit that may resample the received information at a first sampling rate if a high priority is assigned, and resample the received information at a second, lower sampling rate if a low priority is assigned.

In Example 12, the subject matter of any one or more of Examples 1-11 optionally includes the control circuit that may extract a first number of data features from the received information if a high priority is assigned, and extract a second, lower number of data features from the received information if a low priority is assigned.

In Example 13, the subject matter of any one or more of Examples 1-12 optionally includes the control circuit that may extract a first portion of the received information for storage or transmission if a high priority is assigned, and extract a second, smaller portion of the received information for storage or transmission if a low priority is assigned.

In Example 14, the subject matter of Example 13 optionally includes the first portion of the received information that may include received information prior to an onset of the sensed physiological event.

In Example 15, the subject matter of any one or more of Examples 1-14 optionally includes the control circuit that may receive a user selection of a portion of the received information for data storage or data transmission.

Example 16 is a method comprising steps of: receiving via a receiver circuit information about a physiological event sensed from a patient; assigning, via an event prioritizer circuit, a priority to the received information; performing, via a control circuit, a first data reduction of the received information if a high priority indicator is assigned, and a second data reduction of the received information if a low priority indicator is assigned, where the second data reduction has a higher data reduction rate than the first data reduction; and outputting the received information to a user or a process according to the assigned priority via an output circuit, In Example 17, the subject matter of Example 16 optionally includes computing a similarity metric between the received information and information from one or more patient historical physiological events, wherein the priority may be assigned according to the computed similarity metric.

In Example 18, the subject matter of Example 16 optionally includes storing the received information in a data storage circuit according to the assigned priority.

In Example 19, the subject matter of Example 18 optionally includes allocating storage space in the data storage circuit for storing the received information according to the assigned priority.

In Example 20, the subject matter of Example 16 optionally includes steps of: establishing a communication between an ambulatory medical device (AMD) and an external device, the AMD including one or more of the receiver circuit, the event prioritizer circuit, and the control circuit; and transmitting the received information to the external device according to the assigned priority.

In Example 21, the subject matter of Example 20 optionally includes allocating communication bandwidth for transmitting the received information according to the assigned priority.

In Example 22, the subject matter of Example 16 optionally includes the first data reduction including extracting a first number of data features from the received information if a high priority is assigned, and the second data reduction including extracting a second, lower number of data features from the received information if a low priority is assigned.

In Example 23, the subject matter of Example 16 optionally includes the first data reduction including extracting a first portion of the received information for storage or transmission if a high priority is assigned, and the second data reduction including extracting a second, smaller portion of the received information for storage or transmission if a low priority is assigned.

The event priority-based data storage and transmission as discussed in this document may improve functionality of a medical device such as an AMD. As previously discussed, AMDs are usually constrained by battery power, storage space, computing and information processing power, and communication bandwidth, among other device resources. Processing and transmission of medical data associated with device detected physiological events may consume a lot of device power. This may reduce device longevity, and have long-term clinical and economic impact on patient management. The event priority-based data reduction, data storage, and data communication discussed in this document allocate the resources available to an AMD according to clinical significance or diagnostic value of the physiological events detected by the AMD. For example, more storage space and communication bandwidth may be allocated to physiological events indicating more severe condition or of more diagnostic value to a clinician. AMDs implemented with the data management technology as discussed in this document may therefore provide a power- and resource-conservative approach to improve the efficiency of usage of the device power, memory, and communication bandwidth. The device longevity may therefore be extended.

The improved data management in an AMD as discussed in this document may in turn improve patient care through the patient monitoring system coupled to the AMD. A physiological event containing new information may be assigned a higher priority for storage and transmission, and may be timely reviewed by the clinician. As such, patients may receive immediate medical attention. Conversely, a physiological event with a lower degree of severity is assigned a lower priority, and may not take much storage space or exhaust much of the computing resources or communication bandwidth. Therefore, devices and methods discussed herein would better distribute the medical resources to serve the need of more patients at little to no additional cost or system complexity.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for managing medical data storage and transmission. A data management system may receive information about a physiological event sensed from a patient, and assign a priority to the physiological event. The system may perform data reduction according to the assigned priority, such that the received information associated with a lower priority event may be processed with a higher data reduction rate than the received information associated with a higher priority event. The received information may be output to a user or a process, or transmitted to an external device, according to the priority.

Figure 1:
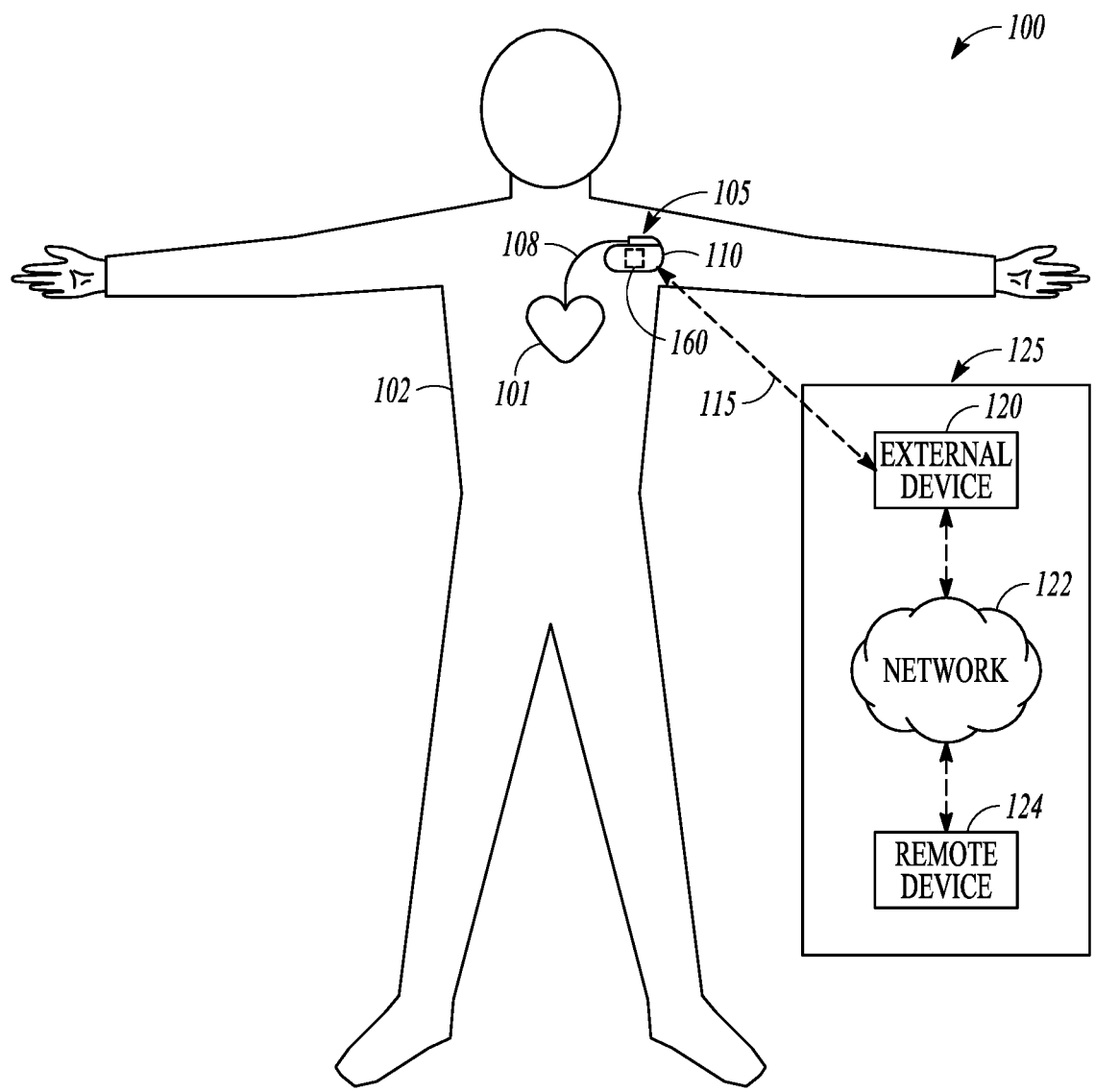
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

In an example, the AMD 110 may include a data management circuit 160 for managing storage and transmission of medical data associated with a physiological event detected from a patient. Examples of the physiological event may include a cardiac arrhythmia such as atrial fibrillation, atrial flutter, atrial tachycardia, supraventricular tachycardia, ventricular tachycardia, or ventricular fibrillation, among other atrial or ventricular brady- or tachy-arrhythmia, a chronic medical condition, such as worsening heart failure (WHF). In another example, the physiological event may include patient-triggered events. The data management circuit 160 may assign a priority to the sensed physiological event, perform data processing and store the medical data in a data storage circuit according to the assigned priority. Additionally or alternatively, the data management circuit 160 may transmit the medical data to an external device according to the assigned priority.

The AMD 110 may alternatively be configured as a therapeutic device configured to treat arrhythmia or other heart conditions. The AMD 110 may include a therapy circuit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring medical data, performing at least one self-diagnostic test (such as for a device operational status), analyzing the medical data to detect a cardiac arrhythmias, or optionally delivering or adjusting a therapy to the patient 102. Additionally, the external system 125 may receive device data from the AMD 110 via the communication link 115. Examples of the device data received by the external system 125 may include real-time or stored medical data from the patient 102, diagnostic data such as detection of cardiac arrhythmias or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. Alternatively or additionally, the alert conditions may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 124, including the server and the interconnected clients, may also execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected physiological events to a system user such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 120 or the remote device 124 may include a respective display unit for displaying the physiological or functional signals, or alerts, alarms, emergency calls, or other forms of warnings to signal the detection of arrhythmias. In some examples, the external system 125 may include an external data processor configured to analyze the physiological or functional signals received by the AMID 110, and to confirm or reject the detection of arrhythmias. Computationally intensive algorithms, such as machine-learning algorithms, may be implemented in the external data processor to process the data retrospectively to detect cardiac arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
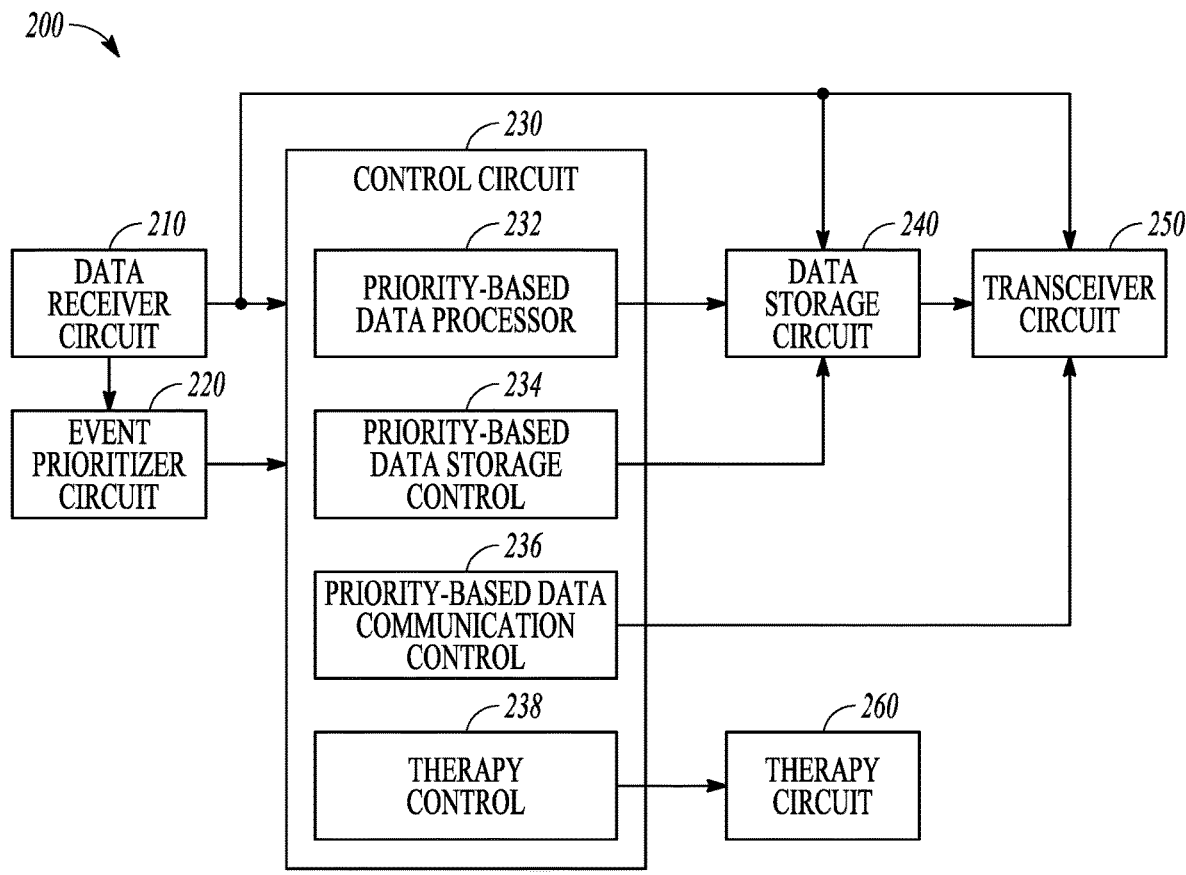
FIG. 2 illustrates generally an example of a data management system for managing storage and transmission of medical data associated with physiological events.

FIG. 2 illustrates generally an example of a data management system 200 for managing storage and transmission of medical data associated with physiological events detected from one or more patients. At least a portion of the data management system 200 may be implemented in the AMD 110, the external system 125 such as one or more of the external device 120 or the remote device 124, or distributed between the AMD 110 and the external system 125. As illustrated in FIG. 2, the data management system 200 may include one or more of a data receiver circuit 210, a n event prioritizer circuit 220, a control circuit 230, a data storage circuit 240, and a communication circuit 250. The data management system 200 may additionally be configured as a therapeutic system that includes an optional therapy circuit 260 for delivering a therapy to treat a disease or to alleviate a medical condition.

The data receiver circuit 210 may be coupled to a sensing circuit to sense information including patient medical data, such as a physiological signal from a patient via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The data receiver circuit 210 may include one or more sub-circuits to digitize, filter, or perform other signal conditioning operations on the received physiological signal.

The received information may be associated with a physiological event detected from the patient. In an example, the data management system 200 may include a detector circuit, coupled to the data receiver circuit 210, to detect a target physiological event from the sensed physiological signals. In some examples, the physiological signals sensed from a patient may be stored in a storage device, such as an electronic medical record (EMR) system. The detector circuit may be configured to receive a physiological signal from the storage device in response to a user input or triggered by a specific event, and detect a target physiological event from the received physiological signals. In an example, the target physiological event may include a cardiac arrhythmia episode. The detector circuit may detect the cardiac arrhythmia using heart rates, heart rate statistics such as heart rate stability or variability, atrio-ventricular activation patterns (e.g., timing relationship between atrial activation and ventricular activation within a cardiac cycle), morphologies of cardiac electrical or mechanical signals, or hemodynamic parameters. In another example, the target physiological event may include worsening chronic medical condition, such as worsening heart failure (WHF). The detector circuit may detect the WHF by detecting a trend of a physiological signal metric, such as one or more of a decrease in thoracic impedance, an increase in respiration rate or a rapid-shallow breathing index (RSBI) computed as a ratio of a respiratory rate measurement to a tidal volume measurement, an increase in intensity or timing of a heart sound component, among others. In some examples, the detector circuit may detect patient-triggered events. This may include, for example, a button push or other actuator means on the AMD 110, a handheld device, or through the user interface when the patient experiences a symptom of an onset, or a precursor, of the target physiological event.

The event prioritizer circuit 220, coupled to the data receiver circuit 210, may be configured to assign a priority to the detected physiological event using the received information. The event prioritizer circuit 220 may be implemented as a part of a microprocessor circuit, which may be a dedicated processor such as a digital signal processor, application specific integrated circuit (ASIC), microprocessor, or other type of processor. Alternatively, the microprocessor circuit may be a general purpose processor that may receive and execute a set of instructions of performing the functions, methods, or techniques described herein.

The event prioritizer circuit 220 may include circuit sets comprising one or more other circuits or sub-circuits. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The event prioritizer circuit 220 may be coupled to the data receiver circuit 210, and configured to assign the priority to the detected physiological event using a comparison of the detected physiological event to one or more patient historical physiological events. The patient historical physiological events may be received from a user, such as via the data receiver circuit 210. Alternatively, the patient historical physiological events may be stored in a data storage device that maintains a database containing information about patient historical physiological events. The information about the historical physiological events may include medical data associated with each of the physiological events in the patient medical history. The medical data in the database may be of the same type as the medical data associated with the detected physiological event. For example, if the receiver circuit 210 receives cardiac electrograms (EGMs) associated with a target cardiac arrhythmia according to a specific sensing vector that include one or more electrodes from the lead system 108, then the stored medical data corresponding to the historical physiological events may also include cardiac EGMs sensed according to the same sensing vector.

The event prioritizer circuit 220 may compare the detected physiological event against the stored information about the historical physiological events, and generate an event priority indicator for the detected physiological event using the comparison. In an example, the event prioritizer circuit 220 may compute a similarity metric between the detected physiological event and the historical physiological events using the medical data associated with the detected physiological event and the stored medical data associated with the historical physiological events. The event prioritizer circuit 220 may generate the event priority indicator by comparing the similarity metric to one or more threshold values or ranges of values. Examples of similarity computation are discussed below, such as with reference to FIG. 3.

The control circuit 230 may include one or more sub-circuits to manage the received information, such as medical data associated with the physiological events. The control circuit 230 may alternatively be implemented as a part of a microprocessor circuit that may receive and execute a set of instructions of performing the functions, methods, or techniques described herein. By way of example and not limitation, the sub-circuits may include one or more of a priority-based data processor 232, a priority-based data storage control 234, or a priority-based data communication control 236 to control data processing, data storage, or data transmission respectively, according to the assigned priority. In some examples, the priority assigned to the physiological events may be presented to a user such as a clinician. The control circuit 230 may receive, such as via a user input device, user selection of a portion of the received medical data for data storage or data transmission.

The priority-based data processor 232 may perform a first data processing of the received medical data if the physiological event is assigned the high priority indicator, or a second data processing of the received medical data if the physiological event is assigned the low priority indicator. The first and second data processing may include data reduction operation. The second data processing includes a higher data reduction rate than the first data processing, such that a physiological even with a lower priority may have a higher amount of data reduction than a physiological even with a higher priority. In an example, the data reduction includes down-sampling operation. The medical data associated with low priority events may be down-sampled at a lower sampling rate than are the medical data associated with high priority events. In an example, the data reduction includes digitizing the received medical data to a lower resolution. The medical data associated with low priority events may be digitized with a lower resolution than are the medical data associated with high priority events.

In another example, the data reduction includes truncating the received medical data, such that a selected portion of the medical data is used for data storage or data transmission. The truncated medical data associated with low priority events may have a shorter duration or data volume than the truncated medical data associated with high priority events. In an example, the selected data portion via the first data processing may include data prior to an onset of the physiological event. Inclusion of such pre-onset data of a high priority event may help a clinician diagnose the physiological event. For example, in syncope detection, cardiac electrical activity signals and other sensor data recorded prior to an onset of a syncope event, when recorded and presented to a clinician, may help the clinician determine triggers or causes or the syncope, such as one of a cardiogenic syncope, an orthostatic hypotension triggered syncope, or a neurally mediated syncope.

In an example, the data reduction includes data feature extraction from the received medical data. The second data processing may result in fewer extracted data features than the first data processing. Therefore, fewer data features may be extracted from the received medical data associated with low priority events than from the medical data associated with high priority events. Example of the data features may include statistical features such as intervals, number of stable or unstable heartbeats, average heart rate, heart rate variability, a signal metric trend, or a rate of range of a signal metric, among others. The data features may include morphological features such as characteristic points of the waveform such as a peak, a trough, an inflection point, or one or more intermediate points between the characteristic points. In an example, data features may be extracted only from the low priority event data, and stored in the data storage circuit 240 or transmitted to an external system such as the external system 125. Medical data associated with high priority event, without being processed with feature extraction, may he stored or transmitted. In an example, the data reduction includes applying a data compression algorithm to the received medical data. The medical data associated with low priority events may be compressed with a higher compression ratio than are the medical data associated with high priority events. In some examples, the data reduction may be achieved by transforming or modeling of the received medical data, and representing the medical data using the transformed data or model parameters.

The data reduction operation may reduce the volume of the medical data to be stored in the storage circuit 240, or to be transmitted to an external system such as the external system 125. Because the high-priority physiological event may be of a higher clinical significance e.g., indicating a more severe health condition or worsening of an existing condition) or of a higher clinical interest (e.g., representing a unprecedented signal characteristic that requires clinician review and adjudication), no or low data reduction may be applied to the medical data associated with the high-priority event so as to substantially preserve the information for clinical review and adjudication. Conversely, low-priority events may not contain much new diagnostic information or be of high diagnostic value to a clinician. For examples, physiological events that resemble patient historical physiological events, particularly those known to be of no or little clinical significance, may not require immediate clinician attention. A higher data reduction of the medical data associated with these low-priority events may save the memory space, communication bandwidth, and other device resources for physiological events with higher priorities.

The priority-based data storage control 234 may controllably store the medical data in a data storage circuit 240 according to the assigned priority. In an example, processed medical data, such as the compressed, down-sampled, truncated, or otherwise transformed medical data generated by the priority-based data processor 232, may be stored in the data storage circuit 240. In an example, the order of data input/output (I/O) to the data storage circuit 240 may be scheduled according to the event priority. For example, the medical data associated with high-priority event may be saved in the data storage circuit 240 before the medical data associated with low-priority event. In another example, the priority-based data storage control 234 may allocate memory space according to the event priority. For example, more memory space may be reserved for high priority events than for low priority events. In an example, the memory may be dynamically allocated if additional high priority events are to be stored in the data storage circuit 240. The memory units in the storage circuit 240 for storing low priority event data may be re-allocated to high priority events. The stored low priority event data may be overwritten by medical data associated with high priority events.

The priority-based data communication control 236 may control data communication such as transmission of the medical data associated with the detected physiological events to an external system. In an example, the system 200 may include an AMD, such as the AMD 110 in FIG. 1. The AMD comprises one or more of the data receiver circuit 210, the event prioritizer circuit 220, or the control circuit 230. The AMD may be operatively in communication with an external system, such as the external system 125 in FIG. 1. The AMD may include a transceiver circuit 250 configured to perform data communication with the external system, including transmitting to the external system the medical data received by the data receiver circuit 210 or the processed data stored in the data storage circuit 240. The transceiver circuit 250 may also receive programming instructions from the external system.

The transceiver circuit 250 may be coupled to the priority-based data communication control 236, which controls transmission of the medical data to the external device according to the assigned priority. In an example, the priority-based data communication control 236 may allocate communication bandwidth according to the assigned priority. For example, more bandwidth may be allocated for transmitting the medical data associated with high priority events than for medical data associated with low priority events. In another example, medical data associated with high priority events may be transmitted prior to the medical data associated with low priority events. The event priority-based control of communication timing, sequence, or bandwidth may help clinicians to timely attend to physiological events with higher clinical significance or of higher clinical interest, such that expert review or clinical intervention may be provided as needed.

The system 200 may include an optional therapy circuit 260 configured to deliver a therapy to the patient. The control circuit 230 may include a therapy control 238 that controls the delivery of the therapy. In an example, the therapy may be delivered in response to the detected physiological event satisfying a specified condition, such as being assigned a high priority. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 260 may modify an existing therapy, such as adjust a stimulation parameter or drug dosage.

Figure 3:
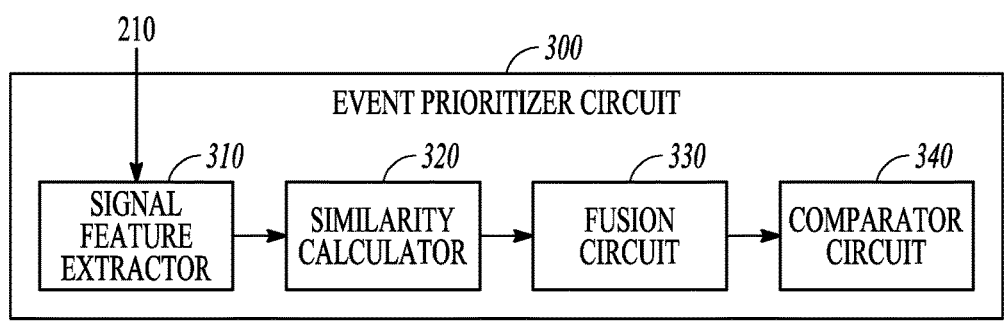
FIG. 3 illustrates generally a block diagram of event prioritizer circuit.

FIG. 3 illustrate generally a block diagram of event prioritizer circuit 300, which is an embodiment of the event prioritizer circuit 220 of the alert management system 200. The event prioritizer circuit 300 may be configured to prioritize a physiological event based on a similarity metric between the detected physiological event and a historical physiological event.

The event analyzer circuit 300 may include a signal feature extractor 310, a similarity calculator 320, a fusion circuit 330, and a comparator circuit 340. The signal feature extractor 310 may extract signal characteristics from the medical data (denoted by Y) associated with a physiological event received from the data receiver circuit 210. The signal feature extractor 310 may additionally extract signal characteristics from the medical data associated with one or more historical physiological events, denoted by $\{X_1, X_2, \ldots, X_N\}$, where N indicates the number of historical physiological events, and $X_i$ represents the stored information corresponding to the i-th historical physiological event.

The signal feature extractor 310 may use the extracted signal characteristics to construct a feature set, denoted by $Y=[Y(1), Y(2), \ldots, Y(M)]$, where M indicates the number of signal characteristics and Y(j) represents measurement of the j-th signal characteristic. The signal characteristics may be generated from multiple data sources such as signals from multiple sensors. Alternatively or additionally, the signal characteristics may represent different statistical or morphological measurements from the same sensor signal. The signal feature extractor 310 may similarly extract from each $X_i$ (for i=1, 2, ..., N) a corresponding feature set, denoted by $X_i=[X_i(1), X_i(2), \ldots, X_i(M)]$, where $X_i(j)$ represents measurement of the j-th signal characteristic of the historical physiological event $X_i$. In an example, the medical data. Y and the stored historical medical data $X_i$ may have different feature dimensions (e.g., Y includes M signal characteristics or features, and $X_i$ include K signal characteristics and $K \ne M$), and Y and $X_i$ include at least one signal characteristic of the same type.

In an example, the detector circuit 220 detects a target physiological event, such as a worsening heart failure (WHF) event, using multiple sensors including, for example, thoracic impedance sensor, heart sound sensor, respiration sensor, cardiac electrical activity sensor, or physical activity sensors, among others. The feature set for the detected physiological event, $Y=[Y(1), Y(2), \ldots, Y(M)]$, includes signal characteristics extracted from different sensors, or from the same sensor. Similarly, the feature set for the i-th historical WHF event (among N historical physiological events), $X_i=[X_i(1), X_i(2), \ldots, X_i(M)]$, may include signal characteristics corresponding to the M signal characteristics in Y. By way of example, if Y(j) represents a thoracic impedance (Z) trend measurement and Y(k) represents a third heart sound (S3) intensity trend measurement corresponding to the detected physiological event, then $X_i(j)$ represents a Z trend measurement and $X_i(k)$ represents a S3 intensity trend measurement corresponding to the i-th historical WHF event.

The similarity calculator 320 may compute a similarity metric between the detected physiological event and each of the historical physiological events $\{X_1, X_2, \ldots, X_N\}$. The similarity metric can include a distance measure between the signal characteristics extracted from the medical data associated with the detected physiological event, and the signal characteristics extracted from the medical data associated with the i-th event, denoted by $d(Y, X_i)$. When both Y and $X_i$ are multi-dimensional feature sets where $Y=[Y(1), Y(2), \ldots, Y(M)]$ and $X_i=[X_i(1), X_i(2), \ldots, X_i(M)]$, the distance $d(Y, X_i)$ may be computed in the multi-dimensional feature space. Examples of the distance can include Euclidean distance, Mahalanobis distance, correlation coefficient, or a L1, L2, or infinite norm, among others.

In some examples, the similarity metric and the event prioritization may be further using the quality of the medical data, such as a signal to noise ratio (SNR), of one or more physiological signals used for detecting the target physiological event. In an example where the similarity metric is a Euclidean distance $d(Y, X_i)$ between Y and $X_i$, the squared differences of individual signal characteristics, such as $(Y(j)-X_i(j))^2$, may each be weighted by the respective SNRs associated with the signal characteristics, that is:

$$d(Y, X_i) = \sqrt{\sum_{j=1}^{M} \alpha_j \cdot (Y(j) - X_i(j))^2}, \text{ for } i=1, 2, \ldots, N \quad (1)$$

where the weight factors $\{\alpha_j\}$ may be proportional to SNR of the physiological signal from which the signal characteristic Y(j) is extracted. A sensor signal with a higher SNR may be more dominant in determining the similarity metric than the sensor signal with a lower SNR. For example, the detector circuit 220 detects the target physiological event using multiple sensors including a thoracic impedance signal and a heart sound signal. The medical data Y=[Y(1), Y(2), . . . , Y(M)] corresponding to the detected physiological event, represented by a multi-dimensional feature vector, includes the Y(j) representing a thoracic impedance trend measurement, and Y(k) representing a S3 intensity trend measurement. If the impedance signal has a higher SNR than the heart sound signal, then in computing the similarity metric between Y and $X_i$, a larger weight may be assigned to the impedance trend measurement than the S3 intensity trend measurement. In some examples, the weight factors $\{\alpha_j\}$ may be determined using the predictive power, or a historical performance, of a physiological signal or signal feature used for detecting the target physiological event. In some other examples, the weight factors $\{\alpha_j\}$ may be user-programmable.

The fusion circuit 330 may use the resultant N similarity metrics, such as distance measures $\{d(Y, X_1), d(Y, X_2), \ldots, d(Y, X_N)\}$, to compute a composite similarity measure representing the similarity between the detected physiological event and the stored historical physiological events. The composite similarity measure may be computed as a weighted combination of the distance measures, that is:

$$D = \sum_{i=1}^{N} w_i \cdot d(Y, X_i) \quad (2)$$

In an example, the weight factors $\{w_i\}$ may be determined according to the temporal proximity of the historical physiological event to the detected physiological event. A more recent historical physiological event such as $X_i$ (temporally proximal to the detected physiological event) may correspond to a larger weight factor $w_i$ than a more remote historical physiological event such as $X_j$ (temporally distal to the detected physiological event). In some examples, the composite similarity measure D may be computed using only a portion of historical physiological events occurring during a specified period of time, such as within a week, a month, or a year prior to the detected physiological event.

The comparator circuit 340 may compare the composite similarity measure D to one or more threshold values, or ranges of values, to categorize the detected physiological event into one of a plurality of predetermined degrees of priority, such as a high priority, medium priority, or low priority. In an example, the assigned priority is inversely related to the similarity metric, such that a lower degree of priority may be assigned to a detected physiological event that is more similar to the historical physiological events, and a higher priority may be assigned to a detected physiological event that is less similar to the historical physiological event. The present inventors have recognized that a detected physiological event that is dissimilar to the historical physiological events may represent a medical condition not seen in patient medical history, or a substantial variation or progression of a historical physiological event that may require immediate medical attention. Assigning a higher priority to such physiological events with unprecedented characteristics may alert the healthcare provider to timely review the detected event, evaluate the patient status, or provide prompt intervention or therapy accordingly. Additionally, such an event prioritization may facilitate timely integration of the newly detected physiological event, optionally along with user adjudication and annotation, into the database of historical physiological events.

In some examples, the information about the historical physiological events may include indicators of severity or clinical significance of the medical events associated with the historical physiological events. The severity indicators may be provided by a clinician. In an example, historical medical events that result in physician intervention or hospitalization may be designated as severe historical physiological events. The comparator circuit 340 may compare the detected medical event to the severe historical physiological events and to other non-severe historical physiological events (such as annotated by a clinician, or those physiological events not resulting in hospitalization or intervention). The comparator circuit 340 may assign a higher priority to a detected medical event that is similar to the severe historical physiological event, or dissimilar to the severe or non-severe historical physiological events, and assign a lower priority to a detected medical event that is similar to the non-severe historical physiological events. The medical events with characteristics similar to severe medical events in patient medical history are likely of clinical significance. Assigning a higher priority to such events may ensure immediate medical attention and intervention as needed. In some examples, the physiological event prioritizer circuit 234 may assign a highest priority to the detected medical event that is similar to the severe historical physiological event, followed by the detected medical event dissimilar to the severe or non-severe historical physiological events, and assign a lowest priority to the detected medical event that is similar to the non-severe historical physiological events.

Figure 4:
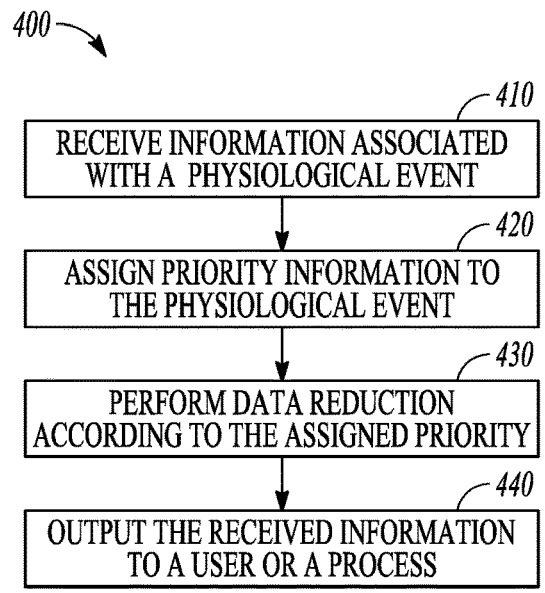
FIG. 4 illustrates generally an example of a method for managing medical data storage and transmission

FIG. 4 illustrates generally an example of a method 400 for managing medical data storage and transmission. The medical data may be associated with physiological events detected from one or more patients. The method 400 may be implemented and executed in an ambulatory medical device such as an implantable or wearable medical device, or in a remote patient management system. In an example, the method 400 may be implemented in, and executed by, the AMD 110, one or more devices in the external system 125, or the alert management systems 200 or 400.

The method 400 begins at 410, where information associated with a physiological event may be received. The received information may include medical data, such as one or more physiological signals received by the data receiver circuit 210. Examples of the physiological signals may include a cardiac electrical signal, such as an electrocardiography (ECG) or an intracardiac electrogram (EGM), thoracic or cardiac impedance signal, arterial pressure signal, pulmonary artery pressure signal, left atrial pressure signal, RV pressure signal, LV coronary pressure signal, heart sounds or endocardial acceleration signal, physiological response to activity, apnea hypopnea index, one or more respiration signals such as a respiration rate signal or a tidal volume signal, among others. The sensed physiological signal may be pre-processed, including one or more of signal amplification, digitization, filtering, or other signal conditioning operations. In some examples, signal metrics such as timing parameters, or statistical or morphological parameters may be detected from the sensed physiological signal. In some examples, contextual data such as time of day, temperature, environmental parameters, or patient medical record information may additionally be received at 410. In some examples, the physiological signals sensed from a patient may he stored in a storage device, such as an electronic medical record (EMR) system.

The medical data received at 410 may be associated with a physiological event such as a cardiac arrhythmia episode, worsening of a chronic medical condition such as worsening heart failure (WHF). The physiological event may be detected from one or more physiological signals. Additionally or alternatively, the detected physiological events may include patient-triggered events, such as when the patient experiences a target physiological event.

At 420, a priority may be assigned to the detected physiological event using the received medical data. In an example, detected physiological event may be compared to one or more patient historical physiological events, and the priority may be determined based on the comparison. The patient historical physiological events, which may be received at 410, may include a database of medical data associated with the physiological events in the patient medical history. The stored medical data may be of the same types as the medical data associated with the target physiological event example, if the physiological event is an arrhythmia episode detected from cardiac electrograms sensed from a specific sensing vector comprising an anode and a cathode, the medical data associated with the historical physiological events may include the cardiac electrograms sensed according to the same sensing vector.

A similarity metric may be computed between the medical data associated with the detected physiological event and the stored medical data associated with the historical physiological events. The similarity metric may include a distance measure such as Euclidean distance, Mahalanobis distance, correlation coefficient, or a L1, L2, or infinite norm, among others. In an example, signal characteristics may be extracted from the medical data associated with the detected physiological event. Similarly, signal characteristics may be extracted from the medical data associated with a historical physiological event. A similarity metric between the feature vector associated with the detected physiological event, and the feature vector of each of the historical physiological event, may be computed. The similarity metric may include a distance in the multi-dimensional feature space. A composite similarity measure may then be computed using the resultant similarity metrics, such as by using the event analyzer circuit 300, as previously discussed with reference to FIG. 3.

An event priority indicator may be assigned to the detected physiological event. In an example, the similarity metric may be compared to one or more threshold values, or ranges of values, and the detected physiological event may be categorized as one of a plurality of predetermined degrees of priority, such as a high priority, medium priority, or low priority. The degree of priority may be inversely related to the similarity metric, such that a lower degree of priority may be assigned to a detected physiological event that is similar to the historical physiological events, and a higher degree of priority may be assigned to a detected physiological event that is dissimilar to the historical physiological events. The detected physiological events that are dissimilar to the historical physiological events may indicate new medical conditions not seen in patient medical history, or a variation or progression of a historical physiological event. Such physiological events may require immediate attention by a healthcare provider.

At 430, data reduction may be performed on the received information according to the assigned priority, such as via the control circuit 230 as illustrated in FIG. 2. For example, the received information (e.g., medical data) may be processed using a first data processing if the physiological event is assigned the high priority indicator, or be processed using a different second data processing if the physiological event is assigned the low priority indicator. The second data processing may include a higher data reduction rate than the first data processing. Examples of data processing performed at 430 may include data compression, data truncation, feature extraction, data storage, or data transmission. At least some of the data processing at 430 is executed according to the assigned priority. As discussed previously, such a priority-based data processing, storage, and transmission may be advantageous as it provides a power- and resource-conservative approach to improve the efficiency of usage of the device power, memory, and communication bandwidth, and can extend device longevity. For example, high-priority physiological event may be of a higher clinical significance (e.g., indicating a more severe health condition or worsening of an existing condition) or of a higher clinical interest (e.g., representing a unprecedented signal characteristic that requires clinician review and adjudication), no or low data reduction may be applied to the medical data associated with the high-priority event so as to substantially preserve the information to ensure quality diagnosis. Conversely, low-priority events may not contain substantially new diagnostic information or be of interest to clinicians for review and adjudication. For examples, physiological events that resemble patient historical physiological events, particularly those known to be of no or little clinical significance, may not require immediate clinician attention. A higher data reduction operation applied to the medical data associated with these low-priority events may save the memory space for storing the event data and save communication bandwidth for transmitting the data to the external system. Examples of priority-based medical data processing, storage, and communication are discussed below, such as with reference to FIG. 5.

At 440, the received information may be presented to a user or a process according to the assigned priority. In an example, a plurality of physiological events detected from a patient may each have their respective priority indicators. The physiological events may be ranked according to specific order, such as a descending order, of the event priority indicators. The prioritized physiological event may be displayed on a display, including the patient medical data associated with the detected physiological event, intermediate measurements or computations such as the signal characteristics, similarity metrics, assigned priority, or one or more historical physiological events that are deemed similar to the detected physiological event, among others. Hard copies of the detection information may be generated. A system user, such as a healthcare provider, may interactively annotate, mark on, or comment on the detected physiological event via an input device. In an example, a system user may adjudicate the detected arrhythmia episodes in an order according to the priority indicators of the arrhythmia episodes. The detected physiological event and the associated medical data, optionally along with the annotations, adjudications, or other user feedback may be integrated into the database of the historical physiological events. In some examples, a recommendation may be generate and provided to the user. The recommendation may include one or more of further diagnostic tests to be performed or therapies to administer. The recommendation may also include system-programming recommendations, such as adjustment of one or more parameters, such as detection parameters that may be used to improve sensitivity or specificity of detecting a target physiological event.

The method 400 may include the optional step for delivering a therapy to the patient in response to the detection of the physiological event, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy may be modified such as by adjusting a stimulation parameter or drug dosage.

Figure 5:
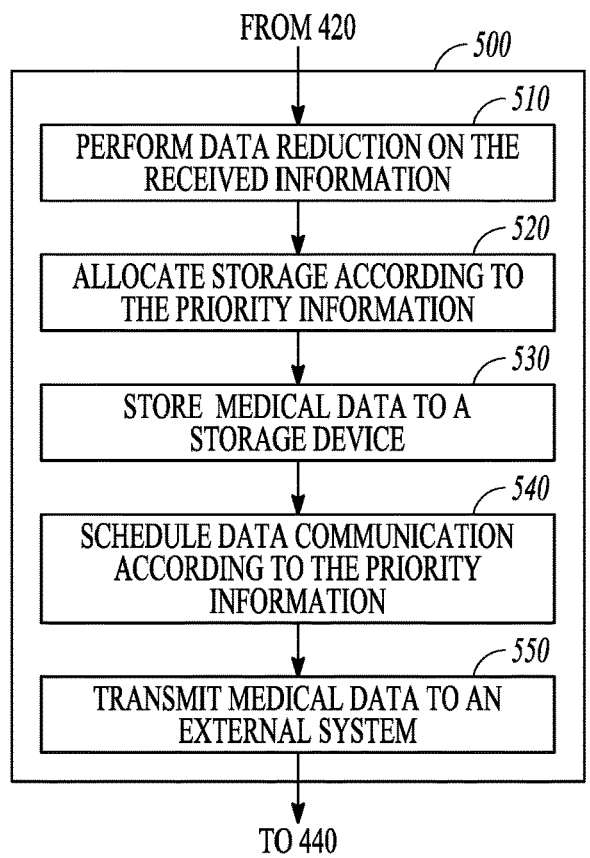
FIG. 5 illustrates generally an example of a method of priority-based data management.

FIG. 5 illustrates generally an example of a method 530 of priority-based data management. The method 530 may be an embodiment of at least a portion of the method 400, including the step 430 for data processing according to the assigned priority.

At 510, data reduction of the received information may be performed, such as by using the priority-based data processor 232. Compared to the high priority events, medical data associated with low priority events may be down-sampled at a lower sampling rate, or digitized with a lower resolution than are the medical data associated with high priority events. In an example, the received medical data may be truncated such that only a portion of the medical data is stored or transmitted to an external system. The truncated medical data associated with low priority events may have a shorter duration or data volume than the truncated medical data associated with high priority events. In some examples, signal feature, including statistical or morphological features, may be extracted from received medical data. Fewer data features may be extracted from the received medical data associated with low priority events than from the medical data associated with high priority events. Additionally or alternatively, the medical data associated with low priority events may be compressed using a data compression algorithm having a higher compression ratio than are the medical data associated with high priority events. For example, the medical data may be transformed or modeled, and represented using fewer data such as the transformed data or model parameters.

At 520, storage space may be allocated for the processed medical data according to the priority, such as by using the priority-based data storage control 234 in the control circuit 230. The order of data input/output (I/O) to the data storage may be scheduled according to the event priority. For example, the medical data associated with high-priority event may be stored before the medical data associated with low-priority event. Additionally or alternatively, more storage space may be allocated for high priority events than for low priority events. In an example, the memory may be dynamically allocated such that some of the memory units originally allocated for storing medical data for low priority events may be re-allocated for high priority events, such that the stored low priority events may be overwritten in the storage device by medical data associated with high priority events. At 530, the processed medical data may be stored in a storage device, such as the data storage circuit 240.

At 540, the stored medical data associated with the detected physiological events may be transmitted to an external system, such as by using the priority-based data communication control 236. In an example, the medical data may be collected, processed, and stored in an AMD, such as the AMD 110 in FIG. 1. A communication may be established between the AMD and the external system, such as the external system 125 in FIG. 1. The data transmission may proceed according to the assigned priority. In an example, communication bandwidth may be allocated proportionally to the assigned priority, such that more bandwidth is allocated for transmitting the medical data associated with high priority events than for medical data associated with low priority events. In another example, medical data associated with high priority events may be transmitted prior to the medical data associated with low priority events. The event priority-based control of communication timing, sequence, or bandwidth may help clinicians to timely attend to physiological events with higher clinical significance or of higher clinical interest, such that expert review or clinical intervention may be provided as needed. At 550, the medical data may be transmitted to the external system, such as via the transceiver circuit 250. The process may then continue at 440 where the physiological event and its associated medical data may be output to a user or a process, such as for clinical review and adjudication.

Figure 6:
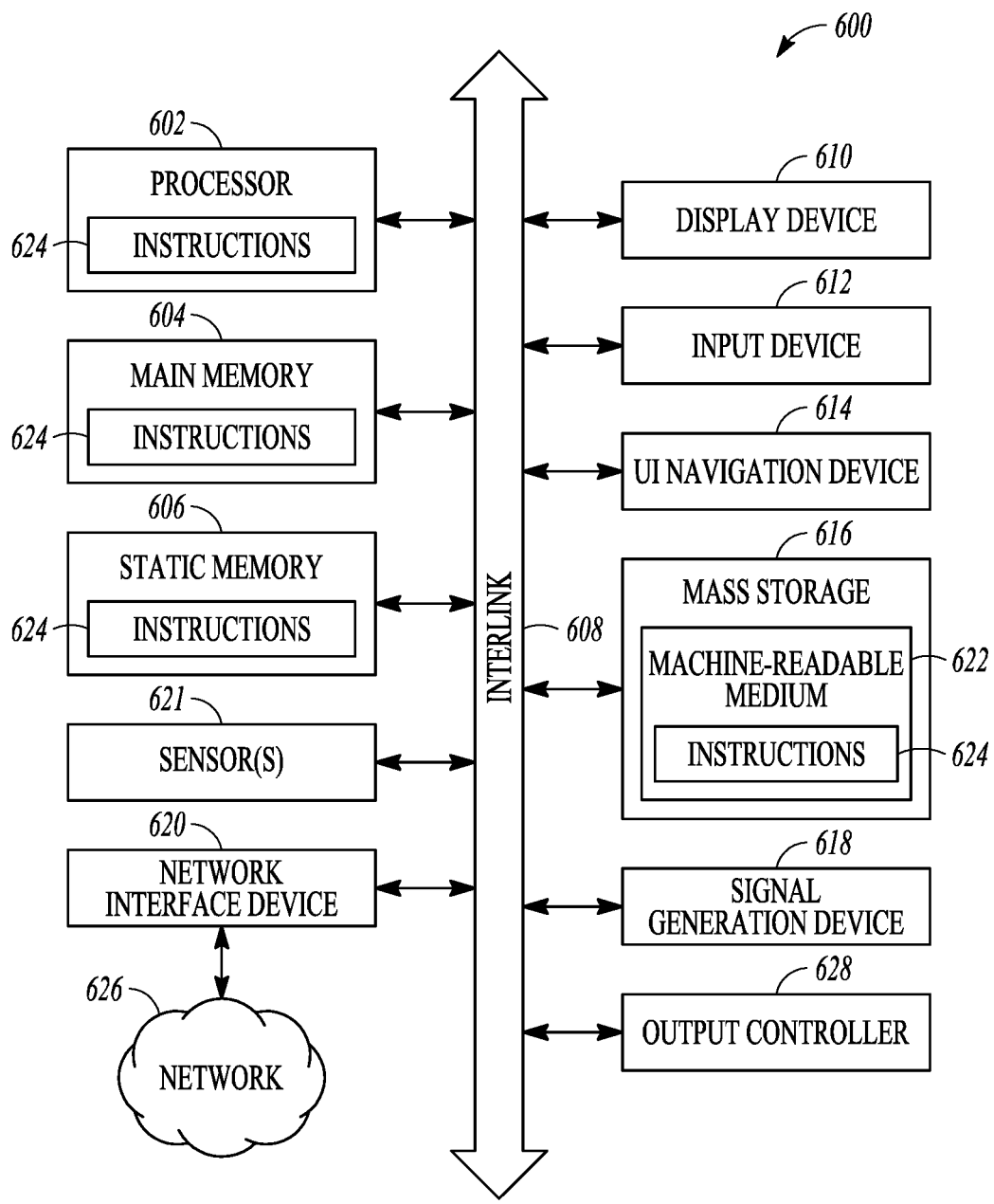
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communication network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communication network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system comprising:
  an ambulatory medical device (AMD) configured to be implanted in or worn by a patient, the AMD comprising:
    a receiver circuit configured to receive physiological information from the patient;
    an event prioritizer circuit configured to:
      detect a first physiological event from the patient using the received physiological information; and
      determine a composite similarity metric using a weighted combination of respective similarities between the detected first physiological event and each of second plurality of physiological events detected from the patient, the second plurality of physiological events each satisfying an alert condition and alerted to a user; and a control circuit configured to:
  a) in response to the composite similarity metric falling below a threshold, generate an alert to the user indicating that the detected first physiological event includes unprecedented physiological information demanding user attention; and
  generate a control signal to a data storage circuit or a transceiver circuit that automatically triggers respective prioritized storage or prioritized communication of the physiological information associated with the detected first physiological event based on the composite similarity metric; and
  b) in response to the composite similarity metric exceeding the threshold, reduce device resource allocation for storing or communicating the received physiological information.

2. The system of claim 1, wherein the event prioritizer circuit is configured to assign a priority to the first physiological event based on the determined composite similarity metric.

3. The system of claim 2, wherein the control circuit is configured to allocate storage space and to store the received information in the data storage circuit according to the assigned priority.

4. The system of claim 2, wherein the AMD is operatively in communication with an external device, wherein the control circuit is further configured to control the transceiver circuit to transmit the received information to the external device according to the assigned priority.

5. The system of claim 2, wherein the control circuit is configured to compress the received information at a first compression ratio if a high priority is assigned, and to compress the received information at a second, higher compression ratio if a low priority is assigned.

6. The system of claim 2, wherein the control circuit is configured to resample the received information at a first sampling rate if a high priority is assigned, and to resample the received information at a second, lower sampling rate if a low priority is assigned.

7. The system of claim 2, wherein the control circuit is configured to extract a first number of data features from the received information if a high priority is assigned, and to extract a second, lower number of data features from the received information if a low priority is assigned.

8. The system of claim 2, wherein the control circuit is configured to extract a first portion of the received information for storage or transmission if a high priority is assigned, and to extract a second, smaller portion of the received information for storage or transmission if a low priority is assigned.

9. The system of claim 2, wherein the receiver circuit is configured to receive an indication of severity or clinical significance of each of the second plurality of physiological events, and the event prioritizer circuit is configured to assign the priority to the first physiological event further using the received indication of severity or clinical significance of each of the second plurality of physiological events of the patient.

10. The system of claim 2, wherein the receiver circuit is configured to receive a user-adjudication of the second plurality of physiological events, and the event prioritizer circuit is configured to assign the priority to the first physiological event further using the received user-adjudication of the second plurality of physiological events.

11. The system of claim 1, wherein the receiver circuit is configured to receive an indication of severity or clinical significance of each of the second plurality of physiological events, and the control circuit is configured to determine if the detected first physiological event satisfies the alert condition further using the received indication of severity or clinical significance of each of the second plurality of physiological events.

12. The system of claim 1, wherein the receiver circuit is configured to receive a user-adjudication of the second plurality of physiological events, and the control circuit is configured to determine if the detected first physiological event satisfies the alert condition further using the received user-adjudication of the second plurality of physiological events.

13. A method of operating an ambulatory medical device (AMD) configured to be implanted in or worn by a patient, the method comprising:
  receiving, via a receiver circuit of the AMD, physiological information sensed from a patient;
  detecting, via an event prioritizer circuit of the AMD, a first physiological event from the patient using the received physiological information;
  determining, via the event prioritizer circuit, a composite similarity metric using a weighted combination of respective similarities between the detected first physiological event and each of second plurality of physiological events detected from the patient, the second plurality of physiological events each satisfying an alert condition and alerted to a user;
  determining, via a control circuit of the AMD, if the detected first physiological event satisfies the alert condition using physiological information of the detected first physiological event and the determined composite similarity metric;
  in response to the composite similarity metric falling below a threshold:
    generating, via the control circuit, an alert to the user indicating that the detected first physiological event includes unprecedented physiological information demanding user attention; and
    generating, via the control circuit, a control signal to a data storage circuit or a transceiver circuit that automatically triggers respective prioritized storage or prioritized communication of the physiological information associated with the detected first physiological event based on the composite similarity metric; and
  in response to the composite similarity metric exceeding the threshold:
    reducing device resource allocation for storing or communicating the received physiological information.

14. The method of claim 13, comprising assigning a priority to the first physiological event based on the determined composite similarity metric.

15. The method of claim 14, comprising receiving a user-adjudication of the second plurality of physiological events, wherein assigning the priority to the first physiological event is further based on the received user-adjudication of the second plurality of physiological events.

16. The method of claim 14, comprising allocating storage space in the data storage circuit and storing the received information according to the assigned priority.

17. The method of claim 14, comprising:
    establishing a communication between the AMD and an external device; and
    transmitting the received information to the external device according to the assigned priority via the transceiver circuit.

18. The method of claim 14, wherein assigning the priority to the first physiological event is further based on an indication of severity or clinical significance of each of the second plurality of physiological events of the patient.

19. The method of claim 13, comprising receiving an indication of severity or clinical significance of each of the second plurality of physiological events, wherein determining if the detected first physiological event satisfies the alert condition is further based on the received indication of severity or clinical significance of each of the second plurality of physiological events.

20. The method of claim 13, comprising receiving a user-adjudication of the second plurality of physiological events, wherein determining if the detected first physiological event satisfies the alert condition is further based on the received user-adjudication of the second plurality of physiological events.

\* \* \* \* \*